United States Patent [19]

Ralet

[11] Patent Number: 4,598,728
[45] Date of Patent: Jul. 8, 1986

[54] PLUGCOCKS

[76] Inventor: Daniel A. C. Ralet, 66, Boulevard Poincare, B-1070 Brussels, Belgium

[21] Appl. No.: 798,144

[22] Filed: Nov. 14, 1985

Related U.S. Application Data

[60] Continuation-in-part of Ser. No. 553,367, Nov. 18, 1983, abandoned, which is a division of Ser. No. 277,355, Jun. 25, 1981, abandoned.

[51] Int. Cl.$^4$ .............................................. F16K 5/02
[52] U.S. Cl. ...................................... 137/15; 137/241; 251/309; 251/368; 99/453
[58] Field of Search ............... 251/312, 311, 310, 309, 251/368; 137/15, 241; 99/452, 453; 426/522

[56] References Cited

U.S. PATENT DOCUMENTS

| | | | |
|---|---|---|---|
| 3,185,179 | 5/1965 | Harautuneian | 251/309 |
| 3,481,367 | 12/1969 | Deuschle | 251/309 |
| 3,698,683 | 10/1972 | De Angelis | 251/309 |
| 3,913,625 | 10/1975 | Gazda et al. | 138/140 |
| 3,913,886 | 10/1975 | Di Cicco | 251/309 |
| 4,003,403 | 1/1977 | Nehring | 251/309 |
| 4,266,754 | 5/1981 | Ninomiya et al. | 251/306 |
| 4,353,763 | 10/1982 | Simons | 138/141 |

FOREIGN PATENT DOCUMENTS 1530115  5/1968  France .

OTHER PUBLICATIONS

Michaud, "PVF$_2$", Modern Plastics Encyclopedia, vol. 51, No. 104, p. 36, Oct. 1974.

Primary Examiner—A. Michael Chambers
Assistant Examiner—John C. Fox
Attorney, Agent, or Firm—Balogh, Osann, Kramer, Dvorak, Genova & Traub

[57] ABSTRACT

The present invention relates to plugcocks or stopcocks, and the method of producing the same. The plugcocks are formed of two primary elements a body and a plug or stem member rotatably mounted therein. The plug member has the shape of a cone the bottom base of which is larger than the top base both the body and the plug or stem being in a plastic material. The invention addresses itself to special problems which arise when a plugcock of plastic material is used in permanent liquid food handling and processing installations such as the milk industry. The problems may include the following: action of heat, rigidity, relative deformations and dilatations. The main characteristic is that the body is at least partly manufactured of PVDF (vynilidene fluoride) and the plug of a thermoplastic which has a rigidity which is maintained at 100° C. The plug may be made of polyolefin selected from the group of polypropylene and polyethylene of high density f.i. of PTFE (polytetrafluorethylene).

6 Claims, 1 Drawing Figure

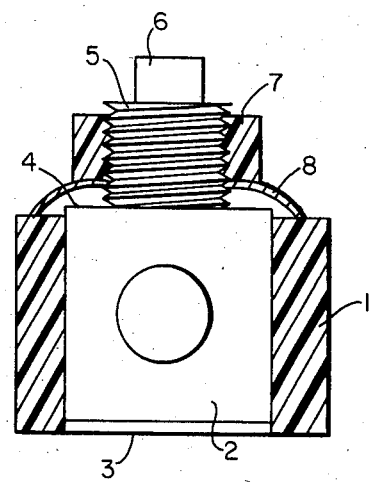

PLUGCOCKS

This application is a continuation-in-part of application Ser. No. 553,367, filed Nov. 18, 1983 now abandoned, which ia a divisional application of Ser. No. 277,355, filed June 25, 1981, also abandoned.

The present invention relates generally to plug-cocks or stop-cocks, and in particular to a plastic thermally undeformable plug-cock assembly mounted in permanent liquid food handling installations, and to the method of producing the same.

The plug-cock assembly is formed of two primary elements, such as a body and a plug or stem member rotatably mounted in the body. Structurally, the plug member has the shape of a cone, the bottom base of which is larger than the top base.

A plug-cock assembly similar in structure is known and is disclosed f.i. by the French Pat. No. 1.530.115 in the name of the applicant and of Claude RALET.

As indicated in this patent, the principle of a stopcock of that kind is to obtain a slight sinking of the plug member under the action of the operator's hand so as to obtain a reduction of the tightening pressure of the plug in the conical inner space of the body.

The annexed figure shows a rotary stopcock assembly including an outer body 1 in which is rotatably disposed a plug member 2 having a bottom base 3 larger than the top base 4.

The plug member 2 is provided at its upper part with a stem 5 terminating by a projection 6 for a handle means (not shown).

The stem 5 is outwardly threaded for cooperation with a nut 7.

The rotating assembly 2-5-6-7 comprises also a spring cup 8.

Stopcocks are known comprising a plastic body and a plastic stem or plug member mounted for rotation within said body and in which the plastic materials are chosen so as to be compatible with the fluid to which they are exposed.

The present invention relates to peculiar problems and difficulties which arise when a plug cock assembly of plastic material is used in permanent liquid food handling or processing installations. The following problems are usually encountered action of heat, rigidity, relative deformation and dilatations are more particularly when the normal operation comprises important temperature differences.

One important observation has been that keeping a satisfactory rigidity at 100° C. is not a sufficient or adequate condition. A great number of plastic materials meet these conditions.

Other necessities are imperative.

The first condition or necessity is to avoid the disastrous consequences for a cock of the kind hereabove indicated involving the thermal deformations to which the plastic materials are particularly sensitive.

In fact the tightness between the cock body and the plug and consequently the possibility of a relative movement at the ordinary temperature have a very little probability to still exist at high temperatures as indeed the dilatation of the plug (male element) must correspond exactly in all directions to the dilatation of the cock-body (female element).

Moreover as regards the majority of the plastic materials, when coming back to the ordinary temperature the dimensions of the piece are not exactly the same as they were existing before the increase of the temperature.

In other words, an increase of temperature and mostly repeated increases of that kind, give birth to some deformations and consequently to a loss of tightness in the cock.

The second condition is the necessity of a smooth sliding between the body and the plug when they are rotated one with respect to the other.

In the practical embodiment of the invention, the body is at least partly manufactured of PVDF (PVF²) and the plug of a thermoplastic which is different but which has a rigidity which is maintained at 100° C.

The PVDF (vynilidene fluoride) is a thermoplastic polymer of general formula

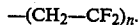

$$-(CH_2-CF_2)_n-$$

The PVDF is manufactured by the Belgian Firm SOLVAY & CY and is known on the registered Trade-Mark name of SOLEF.

As regards the use of PVDF it is to be noted that generally speaking, it has already been suggested to use polyvinylidene fluoride as a valve material.

However the present invention concerns very specially the stopcocks where the problem of coming back to exact initial dimensions after cooling i.e. the indeformability enters into consideration.

As indicated hereabove, the plug may be made in a thermoplastic material which is different but which has a rigidity which is maintained at 100° C. which is the case for polyolefins such as the propylene or polyethylene high density, the polyamids and particularly the polytetrafluorethylene (PTFE).

The PTFE is a polytetrafluorethylene manufactured by E. I. DU PONT DE NEMOURS & CO. INC (U.S.A.) and commercially known under the registered name of TEFLON.

The plug may be executed in PVDF with an addition of PTFE in a proportion not larger than 10%.

It is to be noted that: if f.i. the two materials are the PVDF and the polypropylene, the reverse, i.e. the use of polypropylene for the body and the PVDF for the plug could not give a satisfactory result.

The reason why the PVDF must, according to the invention, be used for the body is caused by a series of properties of the resin:

the characteristic uniformity of its molecule resulting from the polymerisation process and the high crystallinity rate of the material whence results that the internal stresses are not important and consequently that the shrinkages resulting from the cooling are reproductive. This explains why repeated thermal shocks do not give birth to permanent deformations even if the piece does not have the symmetry of a cylinder, which is the case for a cock-body in which the inlet and outlet tubular portions interfere with a cylindrical symmetry;

the fall of the termal dilatation coefficient of the PVDF between the limits of the temperature after 50°-100° C. is an exceptional property the consequence of which is that a cock-body in which periodically hot or boiling water circulates is exposed only to a limited dilatation.

Such a limitation in the dilatation of the cock-body which is a piece larger than a plug renders possible the necessary cooperation and correspondence i.e. the equality between the absolute dilatations of the body and the plug and consequently the maintenance of the tightness and movement possibility. This correspondence is obtained when the plug is made of polypropylene.

It must be noted as regards the plug that its shape is much nearer to cylindrical symmetry than that of the cock and it is reflected in such a manner that the eventual internal tensions in the material generally have no considerable consequence i.e. that no permanent deformations occur. The choice of the material is consequently essentially determined by the coincidence of the dilatation of the plug with the dilatation of the body and by a favorable sliding of the former in contact with the PVDF of the cock-body. The polypropylene material answers those necessities while at the same time being a cheap material.

The good and favorable sliding is a very important property because the tightness is a consequence thereof; it is by this sliding that the plug is adapted to "take its place" in the body in such a manner that the contact between the surfaces is obtained at all points.

This is the reason why it is advantageous to render the PVDF as slippery as possible. This may be obtained by the addition to the PVDF of a proportion of PTFE which possesses an excellent friction coefficient.

The invention covers also use of a cock in which the cock-body is made of pure PVDF and the plug in a composite material PVDF+PTFE or the reverse.

In practice the experience has shown that a cock manufactured in the following manner fully answers the requirements of the invention:

Body: PVDF with addition of PTFE in the proportion of 1 to 10%;

Plug: polypropylene

Spring-cup: the more or less important compression produced by the nut controls the readjustment force of the plug made in polypropylene.

As for the spring-cup, the polypropylene is used in relation to its property to resist the wear of the piece and not the thermal properties.

The present invention has great importance in the use of the above-described plug-cock assembly as a control valve in permanent liquid food processing and handling installations requiring regular and repeated exposure to sterilizing temperatures.

A most popular and commercially successful use of the present invention is in the milk and dairy industry, especially in milk handling and processing installations, where after each milking of the cows an operation of rinsing with boiling water takes place.

In such application rises of temperatures occur constantly when the milk ducts are cleaned and it is imperative that the plug cock be not submitted to permanent deformations resulting from repeated thermic dilatation because in case of such deformations, the tightness would not be maintained.

Traditionally, control valves or plug-cock assemblies, as well as other components used in liquid food handling and processing installations, have had to meet strict standards developed by manufacturers' associations and governmental regulatory agencies.

Stainless steel was one of the few materials approved for manufacture of plug-cocks or valves used in liquid food handling (milk processing) applications. However, it involved a disadvantage due to the extremely high cost involved.

Particularly in the United States, there have been established strict sanitary standards for the type of plastic materials and composition as well as equipment that are approved for use in liquid food handling installations, and in particular milk and dairy processing installations.

Such standards require the plastic materials to be relatively inert, resistant to scratching, scoring, decomposition, crazing, chipping and distortion under normal use conditions, also, non-toxic, fat-resistant, relatively non-absorbent, relatively insoluble, do not release component chemicals or impart flavor or ordor to the processed product, and which maintain their original properties under repeated use conditions (Pasteurized milk, 3-A standard 20-12 MUP).

Since very few plastic materials can meet such strict requirements, plastic materials could not be used satisfactorily in the manufacture of control valves or plug-cock assemblies in the aforesaid industries.

While various forms of plastic valves were sought to be used, it was without much success. Against this background, manufacturers' guide lines and standards committees or governmental regulatory agencies have not listed or identified plastic materials on the list of approved materials.

There has been, therefore, a long-felt need to experiment, test, research and discover the type of plastic material and composition which can meet the standards required for manufacture of the aforesaid plug-cock assemblies.

The applicant-inventor has experimented and tested various plastic materials and discovered a particular combination of plastic materials (having the composition as described and claimed in the instant application) which can fully meet the requirements for control valves in the permanent liquid food processing installations, and especially in the milk handling installations.

In denising the thermally undeformable rotary plug-cock assembly of the present invention, as well as the method of making the same, the applicant-inventor has substantially resolved the long-felt need in the pertaining art, which need was not addressed by others.

The plug-cock assemblies as claimed, generally three-way control valves, are installed in liquid food processing installations, and particularly in milk plants, having been designed for that purpose.

They have been manufactured and used satisfactorily and successfully in Europe since 1978, the thousands and thousands of units sold never having induced any complaints.

There is also great demand and interest in the U.S. dairy and milk industry for using these devices, due to the far higher cost of using metal or stainless steel valves.

However, as related above, American sanitary standards in the pertaining field of use have not (up to the recent surprising development discussed below) listed plastic materials as usable for manufacturing control valves and components for the dairy and milk industry. While plastic material, per se, was not prohibited by the Pasteurized Milk Ordinance, the use of it was subjected to restrictions (for example, only for gaskets, sealing applications and short flexible take-down jumpers or connections where flexibility is required for essential reasons).

However, in a recent development, the Sanitary Standards Committees of the milk industry have changed their position concerning the use of plastic materials in processing equipment and installations. This change of position is based to a large extent on the applicant-inventor's efforts and investment in research and development of the present invention.

The 3-A Sanitary Standards Committees of the Dairy Industry Manufacturers Association have established standards for multiple-use plastic materials used as product contact surfaces for dairy equipment (Number 20-13", July 1, 1985).

The 3-A Sanitary Standards are divided into two groups:

1. One deals with plastic compositions that are already approved for use in the milk and dairy industry. The plastic material compositions as described above are listed on the approved list of materials issued by the 3-A Sanitary Standards Committees.

2. The other deals with apparatus, equipment and components made of the approved plastic materials (included are control valves or plug-cock assemblies). While this group of standards has already been preliminarily approved, it has yet to be officially published and listed (add the approved plastic material to the list including stainless steel products).

It is believed that the new standards will be officially approved around May, 1986.

The standards approved by the 3-A Sanitary Standards Committees are usually approved and adopted by the FDA (Food and Drug Administration) Standards Committees (to be included in amendments to the Pasteurized Milk Ordinance).

Under these new standards, rigid plastic materials (such as the ones described above) may be used in demountable piping, fittings, valves and connections, provided they comply with "3-A standards for multiple-use plastic materials used as product contact surfaces for dairy equipment" [No. 20-12(13)].

Specifically, such plastic materials may be used in valves for parts of which the contact between each other is a condition of tightness, if repeated thermal dilations and shrinkages do not induce permanent deformations being injurious to the tightness condition.

The body and plug members of the rotary plug-cock assembly of the present invention are complying with the above newly-established standards, and satisfactorily meet the requirements as specified by the 3-A Sanitary Standards for multiple-use plastic materials (No. 20-12).

The valves manufactured by applicant have been tested for compliance with the aforementioned standards by the Industriele Hogeschool Van Het Rijk-C.T.L., Gent, Belgium, at the request of Solvay & Cie., S.A. (This chemical concern produces "Solef" PVDF, of which the body or main part of the plug-cock assembly is made).

The tests, being of long duration, having extended over a period of five months, have shown that the present invention meets satisfactorily the aforementioned newly-established standards for the milk and dairy industry.

What I claim is:

1. A process for producing a thermally undeformable plastic rotary plug-cock assembly mounted in permanent liquid food-handling installations requiring regular and repeated exposure to sterilizing temperatures, said process comprising selecting plastic materials for forming a body and a truncated cone-shaped plug member of said plug-cock assembly, which selecting step comprises choosing plastic materials that meet a predetermined high rigidity and size stability characteristic, and a high degree of free and smooth slidability of contacting parts required for said permanent liquid food-handling installations due to regular and repeated exposure of said plug-cock assembly to sterilizing temperatures therein, forming said body and said plug member from said selected plastic materials, said plug member being formed of a material different from said body material, and disposing said plug member rotatably within said body so as to produce said thermally undeformable plastic plug-cock assembly mounted in said permanent liquid food-handling installations, said selected plastic materials comprising substantially of polyvynilidene fluoride for forming said body, and of a thermoplastic material selected from the group consisting of polypropylene, polyethylene of high density, polyamide, and PTFE (polytetrafluorethylene) for forming said plug member.

2. The process according to claim 1, wherein said plastic materials are selected for forming said body so as to comprise polyvynilidene flouride with an addition of PTFE in a proportion of not larger than 10%.

3. The process according to claim 1, wherein said plastic materials are selected for forming said body so as to comprise a composite material PVDF plus PTFE and said plug member so as to comprise PVDF.

4. A process for controlling the flow of milk in a dairy installation, which requires use of a control valve, the contact between components thereof being subject to a condition of tightness, that repeated thermical dilations and shrinkages do not induce permanent deformations being injurious to said condition of tightness therebetween, which process comprises selecting for control of flow of milk in a conduit system of said dairy installation, at least one control valve in the form of a rotary plug-cock assembly comprising a body and a rotatable plug disposed in the body, the contact between said body and plug meeting said condition of tightness, said body being formed substantially of polyvynilidene fluoride, and said rotatable plug being of a truncated-cone shape and formed of a thermoplastic material selected from the group consisting of polypropylene, polyethylene of high density, polyamide, and PTFE (polytetrafluorethylene).

5. A process for controlling the flow of milk in a dairy installation, which requires repeated sterilization procedures calling for flushing with high temperature sterilizing water or steam at frequent and regular time intervals, the process comprising:
selecting the control of milk in a conduit system of said dairy installation, at least one control valve in the form of a rotary plug-cock assembly, having a body formed substantially of polyvynilidene fluoride, and
a rotatable plug disposed in the body, being of truncated-cone shape, and formed of a thermoplastic material selected from the group consisting of:
polypropylene,
polyethylene of high density,
polyamide, and
PTFE (polytetrafluorethylene).

6. A process for construction of a control arrangement providing for passage of fluid from one point in a permanent liquid food processing system to another, and which system requires repeated sterilization procedures calling for flushing with high temperature sterilizing water or steam at frequent and regular time intervals, comprising:
the step of interconnecting in an appropriate conduit,
at least one control valve in the form of a rotary plug-cock assembly, comprising a body formed substantially of polyvynilidene fluoride, and a rotatable plug disposed in the body being of truncated-cone configuration, and formed of a thermoplastic material selected from the group consisting of:
polypropylene,
polyethylene of high density,
polyamide, and
PTFE (polytetrafluorethylene).

* * * * *